United States Patent
Corley

(10) Patent No.: US 6,765,059 B2
(45) Date of Patent: Jul. 20, 2004

(54) POLYMER MATERIAL

(75) Inventor: Brian Corley, Zossen (DE)

(73) Assignee: BioTronik Mess-und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 10/370,230

(22) Filed: Feb. 19, 2003

(65) Prior Publication Data

US 2003/0153685 A1 Aug. 14, 2003

Related U.S. Application Data

(62) Division of application No. 09/614,677, filed on Jul. 12, 2000, now abandoned.

(30) Foreign Application Priority Data

Jul. 14, 1999 (DE) .......................................... 199 33 279

(51) Int. Cl.[7] .......................... A61M 29/00; C08L 77/00
(52) U.S. Cl. .......................... 525/66; 525/69; 525/92 B; 604/96.01; 604/264
(58) Field of Search ................................ 525/92 B, 69, 525/66, 280; 604/96.01, 264; 606/96

(56) References Cited

U.S. PATENT DOCUMENTS

| | | |
|---|---|---|
| 4,427,828 A | 1/1984 | Hergenrother et al. |
| 4,762,890 A | 8/1988 | Strait et al. |
| 4,871,799 A | 10/1989 | Kobayashi et al. |
| 5,185,199 A | 2/1993 | Sawyer et al. |
| 5,213,148 A | 5/1993 | Masumoto et al. |
| 5,267,959 A | 12/1993 | Forman |
| 5,272,236 A | 12/1993 | Lai et al. |
| 5,304,134 A | 4/1994 | Kraus et al. |
| 5,306,246 A | 4/1994 | Sahatjian et al. |
| 5,342,305 A | 8/1994 | Shonk |
| 5,506,298 A | 4/1996 | Paul et al. |
| 5,554,120 A | 9/1996 | Chen et al. |
| 5,565,523 A | 10/1996 | Chen et al. |
| 5,705,565 A | 1/1998 | Hughes et al. |
| 5,747,591 A | 5/1998 | Chen et al. |
| 5,849,846 A | 12/1998 | Chen et al. |
| 6,093,771 A | 7/2000 | Wunsch et al. |

FOREIGN PATENT DOCUMENTS

| | | |
|---|---|---|
| DE | 196 16 075 A1 | 10/1997 |
| EP | 0 362 826 | 4/1990 |
| EP | 0 697 219 A2 | 2/1996 |

*Primary Examiner*—Ana Woodward
(74) *Attorney, Agent, or Firm*—Christie, Parker & Hale, LLP

(57) ABSTRACT

A polymer material, in particular for a medical instrument such as a balloon catheter, is provided. The polymer material comprising a combination at least of a first constituent comprising a partly crystalline polymer and a second constituent for increasing the flexibility of the material, wherein the polymer material is in the form of a polymer alloy, and wherein the first constituent is formed of a polyamide or a polyether block amide and the second constituent is formed at least partly by a thermoplastic elastomer based on polystyrene (TPE-S). A process for producing the polymer material and a medical device incorporating the polymer material are also provided.

24 Claims, No Drawings

POLYMER MATERIAL

CROSS-REFERENCE TO RELATED APPLICATION

This application is a divisional of U.S. application No. 09/614,677, filed on Jul. 12, 2000, now abandond which claims priority on German patent application number 199 33 279.7, filed Jul. 14, 1999, priority of each of which is claimed herein.

FIELD OF INVENTION

The invention concerns a polymer material, in particular for a medical instrument.

BACKGROUND OF INVENTION

In a number of technical areas, but in particular in relation to medical instruments, for example balloon catheters used in interventional cardiology, components of different polymer materials are frequently used in combination with each other. The consideration of which polymer material to use arises out of the different demands which are to be made with regard to the respective components. For example, the demands made on the balloon of a medical balloon catheter are in part different from those made on the stem of the balloon catheter. Although both the balloon and stem portions of the catheter must exhibit sufficient flexibility so that they can be passed through the bloodstream to the vessel to be dilated, the balloon must expand in a defined fashion when subjected to the action of a pressure applied therein, while that is undesirable in the case of the stem.

Numerous conventional polymer materials are known which fulfil the widely varying flexibility and strength requirements for uses of this kind. For example, European patent application EP 0 697 219 A2 discloses a polymer material which is particularly suitable for a medical balloon catheter and which comprises a combination, more specifically a blend, of at least a first constituent consisting of a partly crystalline polymer, and a second constituent for enhancing the flexibility of the material. However, these conventional polymer materials suffer from the disadvantage that components produced therefrom can be connected to components of polymer materials of a different structure only to a limited extent, or with considerable complication and cost. Components of these conventional polymer materials are therefore of only limited suitability for use with components constructed using other polymer materials in a situation requiring a strong connection between the components, as is necessary, for example, in the case of the connection between the stem and the balloon in a balloon catheter. At the least, a considerable amount of complication and a considerable level of additional cost is involved in forming connections between components that are exposed to large mechanical loads. In some cases, it is even necessary to utilize expensive positively locking or adhesive connections.

Accordingly, a need still exists for a polymer material of the kind set forth above, which permits a simple connection between components produced therefrom and components produced from other polymer materials.

SUMMARY OF INVENTION

This invention is directed to a polymer material in the form of a polymer alloy, which is particularly suited for use in a medical instrument such as a balloon catheter. The polymer material comprises a combination of at least a first constituent, comprising a partly crystalline polymer, and a second constituent for increasing the flexibility of the material, wherein the first constituent is formed of a polyamide or a polyether block amide, and the second constituent is formed at least partly of a thermoplastic elastomer based on polystyrene (TPE-S).

In one exemplary embodiment, the polymer material of the invention comprises in a proportion in weight % of at least 30% by weight, and preferably at least 50% by weight of a copolymer of the first constituent and a thermoplastic elastomer based on polystyrene (TPE-S).

In another exemplary embodiment, the polymer material of the invention is characterized in that the proportion of the first constituent is at most 80% by weight.

In still another exemplary embodiment, the polymer material of the invention is characterized in that the proportion of the second constituent is at least 20% by weight.

In yet another exemplary embodiment, the polymer material of the invention is characterized in that the proportion of amide groups is at most substantially 15% by weight.

In still yet another exemplary embodiment, the polymer material of the invention is characterized in that the copolymer is in the form of a graft copolymer with side chains comprising polyamide or polyether amide on a principal chain comprising a thermoplastic elastomer based on polystyrene (TPE-S).

In still yet another exemplary embodiment, the polymer material of the invention is characterized in that the thermoplastic elastomer based on polystyrene (TPE-S) is formed of a styrene-butadiene-styrene copolymer (SBS), a styrene-ethene butene-styrene copolymer (SEBS), a styrene-isoprene-styrene copolymer (SIS) or a styrene-ethene propene-styrene copolymer (SEES).

In still yet another exemplary embodiment, the polymer material of the invention is characterized in that at least a part of the thermoplastic elastomerbased on polystyrene (TPE-S) of the second constituent is grafted with a compatibilizer, in particular maleic acid anhydride.

In still yet another exemplary embodiment, the polymer material of the invention is characterized in that the proportions of the constituents are matched to each other for connecting the polymer material to polyolefins, in particular polyethylene, by a connection involving joining of the materials.

In still yet another exemplary embodiment, the invention is directed to a process for forming a polymer material characterized in that at least a first constituent formed of a polyamide or a polyether block amide and a second constituent formed of a thermoplastic elastomer based on polystyrene (TPE-S) are reactively compounded to form a copolymer.

In still yet another exemplary embodiment, the invention is directed to a process for forming a polymer material characterized in that the reactive compounding operation is effected in a co-rotating twin-screw extruder, which in particular is optimized for a maximum shearing action.

In still yet another exemplary embodiment, the invention is directed to a process for forming a polymer material characterized in that the reactive compounding operation is effected in such a way that essentially all starting products are substantially completely consumed.

In still yet another exemplary embodiment, the invention is directed to a process for forming a polymer material characterized in that after the extrusion operation the polymer material is subjected to an irradiation cross-linking procedure, in particular by means of gamma radiation.

In still yet another exemplary embodiment, the invention is directed to a medical balloon catheter characterized in that its stem and/or its balloon is produced from a polymer material as set forth above.

In still yet another exemplary embodiment, the invention is directed to a medical balloon catheter characterized in that its balloon is welded to the distal catheter stem and/or the inner tube by a connection involving intimate joining of the materials concerned.

DETAILED DESCRIPTION OF INVENTION

The present invention is directed to a polymer material, in particular for a medical instrument such as a balloon catheter, comprising a combination at least of a first constituent comprising a partly crystalline polymer, and a second constituent for increasing the flexibility of the material, the polymer material being characterized in that it is in the form of a polymer alloy, wherein the first constituent is formed of a polyamide or a polyether block amide, and the second constituent is formed at least partly by a thermoplastic elastomer based on polystyrene (TPE-S). The polymer of this invention affords a material which can be simply connected to other materials, in particular polyolefinic polymer materials.

In a preferred embodiment, the polymer alloy consists at least partially of a copolymer. In such an embodiment, the proportion of copolymer in the polymer alloy is substantially at least 30% by weight, and further preferably substantially at least 50% by weight, whereby the advantageous influences of the copolymers are particularly apparent.

The polymer alloy of the invention is distinguished over conventional polymer blends in which there are no irreversible covalent bonds between the various constituents, by virtue of the high proportion of block and graft copolymers of the two constituents used. Such block and graft copolymers are deposited at the phase interfaces between the two constituents of the alloy and, by virtue of a reduction in the interfacial surface tension, permit finer phase distribution of the two alloy constituents with better force and deformation transmission between the phases and stronger adhesion of the phases to each other. By virtue of the improvement in the interface interactions, alloying of the first and second constituents also permits a combination of two polymer constituents which are thermodynamically highly incompatible, as is the case with the polar polyamide or polyether block amide as the first constituent, and the non-polar thermoplastic elastomers based on polystyrene as the second constituent. A conventional blend of the components specified would yield a polymer material having unsatisfactory mechanical properties, which would not be suitable for the specified uses.

As described above, a preferred embodiment of the polymer alloys according to the invention is distinguished by a particularly high proportion of graft copolymers (theoretically more than 60% of the total volume of the polymer alloy) which comprise a principal chain consisting of the thermoplastic elastomer based on polystyrene, with grafted-on polyamide or polyether block amide branches. In such an embodiment, the polyamide or polyether block amide first constituent ensures good shapability of the polymer material, allowing the formation of a variety of components, as well as adequate strength of the material for a variety of uses, such as, for example, tubular balloons for medical balloon catheters. Accordingly, the thermoplastic polystyrene-based elastomer not only reduces the stiffness of the material or enhances its flexibility, but by virtue of its good to very good adhesion to other polymer materials, affords improved adhesion of a component comprising the material according to the invention to a component comprising other polymer materials, in particular polyolefinic polymer materials, e.g., polyethylene (PE) and polypropylene (PP), but also to other polymer materials, e.g., polystyrene (PS), acrylonitrile-butadiene-styrene (ABS), polyamide (PA), polybutylene terephthalate (PBT), and polyphenylene oxide (PPO). In such an embodiment, good compatibility with polyolefins is due to the polyolefinic soft phase which forms the matrix of those styrene block copolymers.

Besides the mechanical properties of a cross-linked elastomer, which are desirable in terms of enhancing elasticity and impact strength, the use of such a thermoplastic elastomer also affords the advantage of enhancing the thermoplastic workability of the polymer material. The workability of the polymer material permits a component comprising the polymer material according to the invention to be easily connected to a component comprising the same or another polymer material, by at least local fusion of the component comprising the polymer material according to the invention, or both components, in the region of the connection.

Depending on the desired stiffness, the thermoplastic polystyrene-based elastomer used is preferably a styrene-butadiene-styrene copolymer (SBS), a styrene-isoprene-styrene copolymer (SIS), a styrene-ethene butene-styrene copolymer (SEBS), or a styrene-ethene propene-styrene copolymer (SEPS), the latter two being distinguished by a higher level of stiffness than the former. The polyamide used is preferably PA6, PA66, PA11 or PA12, with the former two being distinguished by a higher level of strength and a higher modulus of elasticity.

In preferred embodiments of the polymer material according to the invention, the first constituent is present in a substantial amount up to at most 80% by weight, based on the total amount of first and second constituents. The second constituent is present in an amount of at least 20% by weight. These relative proportions ensure that the above-discussed advantageous influences of the thermoplastic polystyrene-based elastomer on the properties of the material.

The graft copolymers which distinguish these polymer alloys from normal blends are formed in the reactive compounding process with which the polymer alloy is produced. Reactive compounding is typically effected under the action of high shearing and stretch forces, preferably in a co-rotating twin-screw extruder which is optimized by virtue of suitable screw design for maximum mixing and distribution effect. Accordingly, the two constituents of the polymer alloy according to the invention are selected to be highly suitable for the formation of graft copolymers by virtue of the selection of chemical groups which are capable of reaction with each other in such a reactive compounding process.

In the case of the first constituent the reactive group is a terminal amino group (in the case of PA6, PA66, PA11, PA12, the hard phase of the polyether block amides) or a terminal alcohol group (in the case of the soft phase of the polyether block amides).

In the case of the second constituent, the thermoplastic polystyrene-based elastomers, the reactive group is preferably introduced by grafting, in particular peroxidically catalyzed grafting. All graftable groups which are capable of reaction with an amine or an alcohol, such as, for example, acid groups, acid anhydrides, and epoxy groups, are suitable for this purpose. The preferred grafted group for a styrene block copolymer is maleic acid anhydride (MAH). Suitable MAH-functionalized styrene block copolymers of styrene-ethene/butene-styrene type are marketed by Shell Chemical under the designation Kraton FG. Polymers which are functionalized by grafting afford a higher level of functionality than those which are only terminally functional polyamides or polyether block amides. Therefore, it may be sufficient for only a part of the styrene block copolymers in the polymer alloy to be functionally adapted in that way.

In preferred embodiments of the invention, the proportions of the constituents of the polymer material are matched such that the polymer material according to the invention has a strong structural similarity to polyolefins, thereby ensuring that components produced from the polymer material according to the invention can be connected to components produced from polyolefins, in particular polyethylene, by a connection involving joining of the actual materials involved. In such embodiments, the connection involving joining of the materials involved can be afforded by welding to the polyolefin, in particular polyethylene. In such an embodiment, the structural similarity is based on the second constituent of the polymer material, the thermoplastic elastomer, which as a styrene block copolymer has a polyolefinic soft phase. The structural similarity is particularly great if, in accordance with the invention, the main constituent of the polymer material is a graft copolymer with the main chain comprising a styrene block copolymer which has a polyolefinic soft phase. Utilizing such a polymer composition, it is possible to readily connect a component comprising the polymer material according to the invention to a component comprising a polyolefin, in particular polyethylene. This ready connection between the polymer material of the invention and polyolefins is important since polyolefins, in particular polyethylene, are materials which are also frequently used in medical engineering by virtue of the wide latitude of their properties, which are adjustable, particularly in the case of polyethylene, by way of the degree of cross-linking. Accordingly, the constituents of the polymer material are preferably matched to each other in such a way that the proportion of amide groups, which is characteristic for polyolefin-incompatible polyamide materials, is at most substantially 15% by weight. Utilizing a polymer material having such a proportion of amide groups yields a polymer having a polyolefinic or polyolefin-like character, which is adequate for a good connection to polyolefins such as polyethylene.

As already mentioned, the polymer material according to the invention can be made in the form of a polymer alloy, and also in the form of a copolymer comprising the stated constituents. In either case, the polymer material can be produced in accordance with known processes for the production of such alloys or copolymers.

The present invention further concerns a process for producing the polymer material according to the invention, the process being distinguished in that at least a first constituent, formed of a polyamide or a polyether block amide, and a second constituent, formed of a thermoplastic elastomer based on polystyrene, are reactively compounded with each other to form a copolymer, preferably a graft copolymer. In such an embodiment, the reactive compounding procedure is preferably effected by subjecting the constituents to the action of high shearing forces. In such a process the high shearing forces can be effected by placing the components in a co-rotating twin-screw extruder. In such an embodiment, the extruder is preferably optimized to a maximum mixing action, that is to say to a maximum shearing effect. Because the reaction rate is induced by the high shearing forces applied between the functional groups of the compounded constituents maximizing the mixing action further maximizes the reaction rate, which further maximizes the connection between the constituents allowing for the formation of a graft copolymer.

In one preferred embodiment of the process according to the invention, a thermoplastic polystyrene-based elastomer is grafted with a compatibilizer, in particular maleic acid anhydride, to produce a copolymer from the constituents in a particularly simple manner.

The process parameters involved in the reactive compounding operation are preferably selected or adjusted so that essentially all starting products are substantially completely consumed. This selection not only ensures that production of the polymer material according to the invention involves the production of the smallest possible amount of waste, but also ensures that the polymer material is of the desired composition, which arises out of the relationship between the starting products.

The present invention further concerns a balloon for a medical balloon catheter, as well as a medical balloon catheter whose stem, and additionally or alternatively, whose balloon, is produced from a polymer material according to the invention. In this embodiment, the balloon preferably comprises a polymer material according to the invention, and the distal catheter stem and, additionally or alternatively, the inner tube, comprise polyethylene. In a further preferred feature, the catheter stem and, additionally or alternatively, the inner tube, are welded to the balloon in a connection involving fusion joining of the materials involved.

Other advantageous developments of the invention are characterized in the appended claims or are set forth in greater detail hereinafter together with the description of the preferred embodiment of the invention.

A preferred embodiment for the polymer material according to the invention, and a component produced therefrom, represents a balloon for a semi-compliant PTCA-catheter which is essentially produced from a graft copolymer comprising a first constituent and a second constituent. In such an embodiment, the first constituent is formed of a polyamide, more specifically polyamide 12 (PA12), while the second constituent comprises a thermoplastic elastomer based on polystyrene, which is grafted with a compatibilizer. In such an embodiment, the thermoplastic polystyrene-based elastomer is a styrene-ethene butene-styrene copolymer (SEBS) and the compatibilizer used is maleic acid anhydride (MAH).

For producing the polymer material used in the example described herein, a mixture of 80% by weight of polyamide 12 (Grilamid L 25 from Ems Chemie GmbH, 50933 Cologne, DE) and 20% by weight of styrene-ethene butene-styrene copolymer, which in turn is grafted with 1.7% by weight of maleic acid anhydride (Kraton FG 1901 X from Deutsche Shell Chemie GmbH, 65760 Eschborn, DE), is reactively compounded in a co-rotating twin-screw extruder (ZSK 25 from Werner & Pfleiderer).

Under such processing, the maleic acid anhydride, which is grafted onto the styrene-ethene butene-styrene copolymer by virtue of reaction of its acid anhydride group with the terminal amino group of the polyamide chain with the formation of a maleimide bridge, produces a covalent bond between the styrene-ethene butene-styrene copolymer chain and the polyamide chain. This bond causes polyamide chains to be grafted as side chains onto the styrene-ethene butene-styrene principal chain.

An alternative embodiment of the polymer material according to the invention, having the same ratio of polyamide 12 to the styrene-ethene butene-styrene copolymer, is obtained if only half of the styrene-ethene butene-styrene copolymer is maleic acid anhydride-grafted. To produce this variant, a mixture of 80% of polyamide 12 (Grilamid L25), 10% of maleic acid anhydride-grafted styrene-ethene butene-styrene copolymer (Kraton FG 1901 X) and 10% of non-grafted styrene-ethene butene-styrene copolymer (Kraton G 1652 X) is reactively compounded in the above-mentioned mixing unit. In such an embodiment, the process parameters are selected so that the reactive constituents are substantially completely used up in the compounding procedure, yielding a polymer material which essentially comprises a graft copolymer, which is substantially composed of the reactive educts.

The theimoplastically processable polymer material obtained utilizing such a process can then be used in any known fashion to manufacture a balloon for a semi-compliant PTCA-catheter. On example is extrusion of a semi-finished article which is then subjected to further processing in a microballoon-forming process. Besides the highly advantageous mechanical properties, such as high flexibility and adequate strength under the required bursting pressures (depending on the respective balloon diameter, at least between 12 and 14 bars), the balloon produced is distinguished insofar as it can be readily connected by welding to a polymer, such as, for example, polyethylene, in a connection involving intimate joining of the materials.

In another embodiment, particularly with high proportions of SEBS in the alloy, the strength of the material can be further enhanced by subsequent irradiation cross-linking of the extruded semi-finished article prior to the balloon shaping procedure. In this embodiment, the irradiation can be, for example, gamma ray irradiation. It will be appreciated moreover that irradiation cross-linking can also be employed when using other polystyrene based thermoplastic elastomers. It will also be appreciated that irradiation cross-linking can also be used in relation to any semi-finished products comprising the material according to the invention, not just for balloon manufacture.

Utilizing the polymer material as described above allows for the production of a particularly versatile balloon which can also be rapidly connected without difficulty to a variety of catheter stems comprising various polymer materials. The polymer material of the invention is further distinguished from conventional polymer materials by its advantageous mechanical properties and by its high level of resistance to chemicals, both of which make it particularly suitable for medical instruments, and in particular for balloons of balloon catheters. Furthermore, the polymer material allows for inexpensive manufacture and processing of medical devices.

The invention is not limited in terms of implementation thereof to the preferred embodiment set forth hereinbefore, and in particular, it is not limited to use for a medical instrument. On the contrary, a number of variants are possible which make use of the configurations set forth even in forms of a basically different kind.

What is claimed is:

1. A balloon for a balloon catheter, comprising:
a polymer alloy including
a first constituent formed of a polyamide or a block copolymer of polyether and polyamide; and
a second constituent formed at least in part of a thermoplastic elastomer based on polystyrene (TPE-S);
wherein said polymer alloy is at least in part in the form of a graft polymer having a principal chain comprising said second constituent and at least one side chain comprising said first constituent.

2. The balloon as set forth in claim 1 wherein the graft polymer comprises at least 30% by weight of the polymer alloy.

3. The balloon as set forth in claim 1 wherein the graft polymer comprises at least 50% by weight of the polymer alloy.

4. The balloon as set forth in claim 1 wherein the graft polymer comprises at least 60% by weight of the polymer alloy.

5. The balloon as set forth in claim 1 wherein the thermoplastic elastomer based on polystyrene (TPE-S) is formed of a copolymer selected from the group consisting of styrene-butadiene-Styrene copolymers (SBS), styrene-ethene butene-styrene copolymers (SEBS), styrene-isoprene-styrene copolymers (SIS), and styrene-ethene propene-styrene copolymers (SEPS).

6. The balloon as set forth in claim 1 wherein the first constituent comprises up to 80% by weight of the polymer alloy.

7. The balloon as set forth in claim 1 wherein the second constituent comprises at least 20% by weight of the polymer alloy.

8. The balloon as set forth in claim 1 wherein at least a part of the second constituent is grafted with a compatibilizer, and wherein the compatibilizer is maleic acid anhydride.

9. The balloon as set forth in claim 8 wherein the polyamide is PA12, the thermoplastic polystyrene-based elastomer is a styrene-ethene butene-styrene copolymer and the compatibilizer is maleic acid anhydride.

10. The balloon as set forth in claim 8 wherein the polymer alloy comprises a mixture by weight of the polymer alloy of 80% polyamide and 20% thermoplastic elastomer, wherein the thermoplastic elastomer is grafted with 1.7% compatibilizer by weight of the thermoplastic elastomer.

11. The balloon as set forth in claim 8 wherein the polymer alloy comprises a mixture by weight of the polymer alloy of 80% polyamide and 20% thermoplastic elastomer, wherein 50% of the thermoplastic elastomer is grafted with 1.7% compatibilizer by weight of the thermoplastic elastomer, and 50% of the thermoplastic elastomer is non-grafted.

12. The balloon as set forth in claim 1 wherein the first constituent comprises up to 15% by weight of the polymer alloy.

13. The balloon as set forth in claim 1 wherein the polymer alloy has been crosslinked.

14. The balloon as set forth in claim 1 wherein the polyamide is selected from the group consisting of: PA6, PA66, PA11, and PA12.

15. The balloon as set forth in claim 1 wherein the polymer alloy is formed by reactive compounding.

16. The balloon as set forth in claim 1 wherein the balloon is formed by extrusion of a semi-finished article followed by microballoon-forming.

17. The balloon as set forth in claim 16 wherein the semi-finished article is crosslinked before the step of microballoon-forming.

18. The balloon as set forth in claim 1 having a bursting pressure at least between 12 and 14 bars.

19. The balloon as set forth in claim 1 wherein the polymer alloy is radiation crosslinked.

20. The balloon as set forth in claim 19 wherein the radiation is gamma ray radiation.

21. The balloon as set forth in claim 1 wherein the polymer alloy comprises a 1:1 ratio of the polyamide to a styrene-ethene butene-styrene copolymer (SEBS).

22. A medical balloon catheter comprising:
a balloon as set forth in claim 1; and
a stem having at least one inner tube disposed therein; wherein the balloon is coupled to at least one of the stem and the inner tube.

23. The medical balloon catheter as set forth in claim 22 wherein at least one of the stem and inner tube is produced from polyethylene.

24. The medical balloon catheter as set forth in claim 23 wherein the balloon is welded to at least one of the stem and the inner tube by a connection involving intimate joining of the materials.

* * * * *